United States Patent [19]

Glass

[11] Patent Number: 4,928,153
[45] Date of Patent: May 22, 1990

[54] OPTICAL MEASUREMENT OF PARTICLE CONCENTRATION

[75] Inventor: Alexander J. Glass, Ann Arbor, Mich.

[73] Assignee: KMS Fusion, Inc., Ann Arbor, Mich.

[21] Appl. No.: 34,995

[22] Filed: Apr. 6, 1987

[51] Int. Cl.$^5$ .................. G01N 21/27; G01N 15/06
[52] U.S. Cl. ............................................. 356/343
[58] Field of Search ............... 356/38, 336, 338, 341, 356/343

[56] References Cited

U.S. PATENT DOCUMENTS

| | | | |
|---|---|---|---|
| 3,724,951 | 4/1973 | Seelbinder | 356/343 X |
| 4,047,815 | 9/1977 | Sedlacek | 356/343 X |
| 4,621,063 | 11/1986 | Wyatt et al. | 356/38 X |

Primary Examiner—Davis L. Willis
Assistant Examiner—Matthew W. Koren
Attorney, Agent, or Firm—Barnes, Kisselle, Raisch, Choate, Whittemore & Hulbert

[57] ABSTRACT

Method and apparatus for measuring concentration of micrometer- and submicrometer-size particles on a carrier as a function of Mie scattering in the visible spectrum. A collimated beam of white light is directed through a carrier onto the particles, with a portion of the light energy being scattered and a portion transmitted according to Mie scattering theory. Particle size, index of refraction and measurement wavelength are selected such that scattering extinction varies essentially monotonically with the ratio of particle size to illumination wavelength. Particle concentration is indicated as a function of a difference between light scattered at two wavelengths at opposite ends of the visible spectrum.

17 Claims, 2 Drawing Sheets

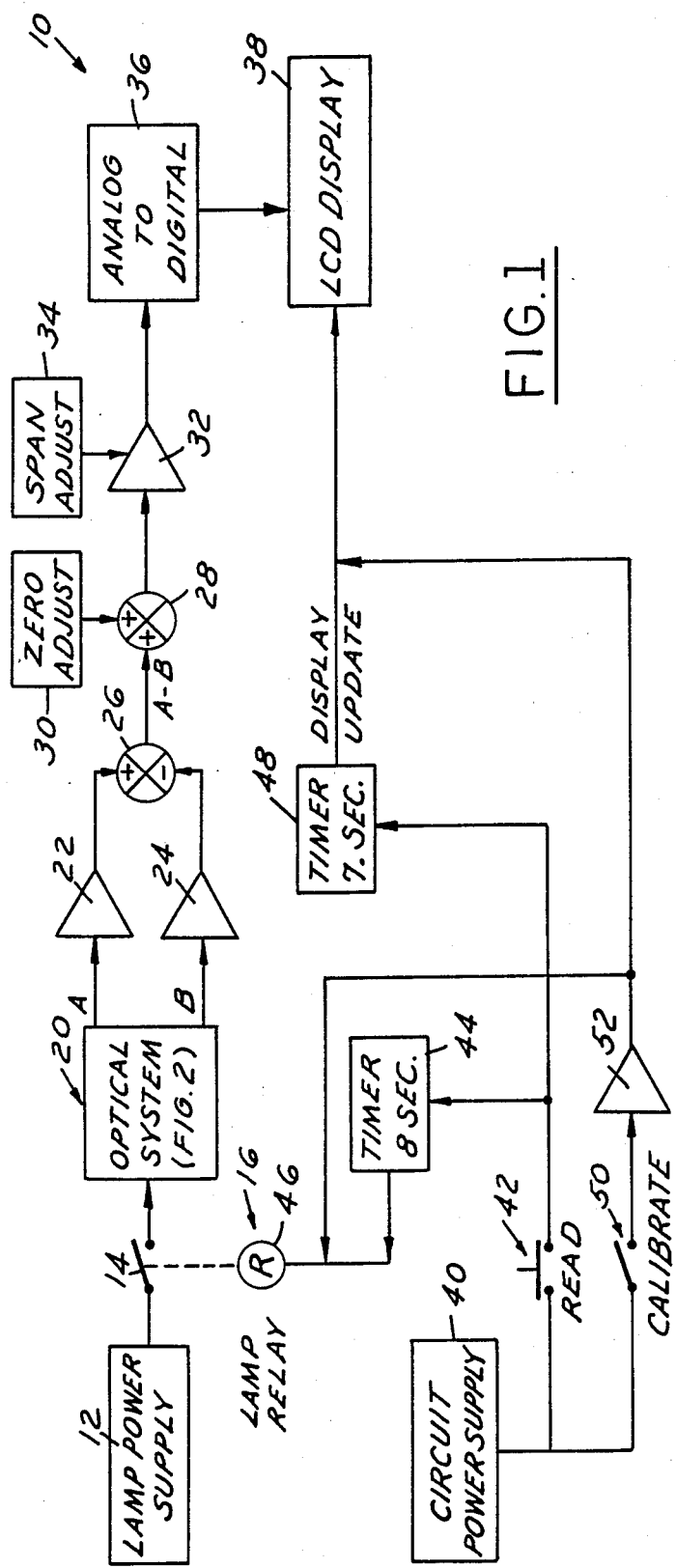
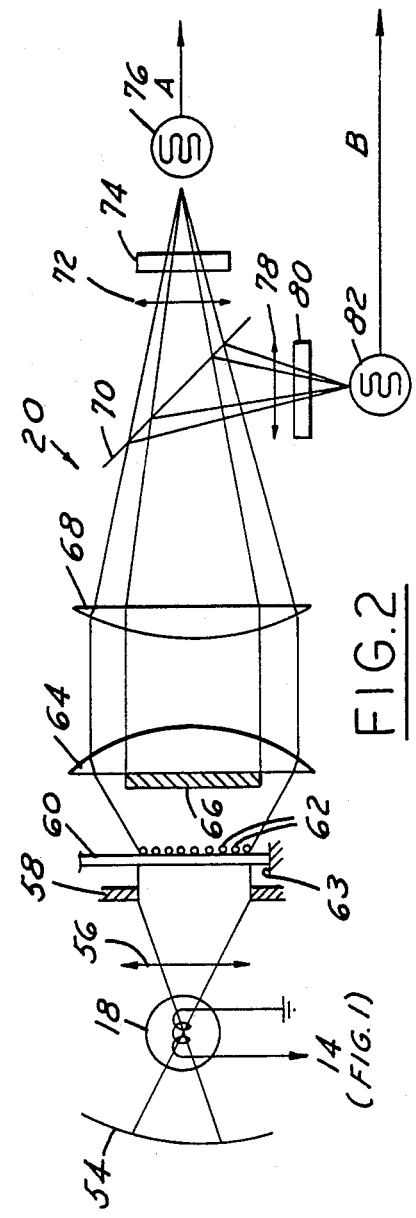
FIG.1
FIG.2

OPTICAL MEASUREMENT OF PARTICLE CONCENTRATION

The present invention is directed to measurement of concentration of particles of a size on the same order of magnitude as the wavelengths of visible light, and more particularly to a method and apparatus for measuring surface concentration of an essentially monodisperse distribution of submicron-size particles on a translucent or reflecting carrier.

BACKGROUND AND OBJECTS OF THE INVENTION

Copending application Ser. No. 898,874 filed Aug. 20, 1986 and entitled "Biologically Active Material Test", now U.S. Pat. No. 4,716,123, discloses a technique for measuring concentration of antigen molecules in a test sample. A multiplicity of spherical latex particles and a dipstick or slide, both of which are surface-pretreated to be biologically active, are placed in a solution containing the test sample. Antibodies on the surfaces of the dipstick and particles react with antigens in the solution and bond the particles to the surface of the dipstick. The concentration or density of particles on the surface of the dipstick, measured as the number of particles per unit area, is thus a measure of antigen concentration in the test solution. Time required to complete a test is a function, in part, of rate of diffusion of particles in solution, which in turn is a function of particle size. Ability to measure concentration also varies with particle size. In a compromise between test speed and measurability, a particle size of less than 1 μm, and particularly in the range of 300 to 500 nm, is presently preferred. For purposes of calibrating the test procedure, it is also preferable that the test particles have an essentially monodisperse size distribution—i.e., of preselected uniform size ±10%.

According to conventional practice, the density of particles attached to the surface of the capture strip or dipstick is determined by visual inspection by a trained operator, and a subjective score ranging from 0 for a blank strip to 5 for a full strip is assigned to the test strip depending upon observed particle density. For a well-trained technician, substantial correspondence can be obtained between such visual assignments, termed visual immuno-assay (VIA) scores, and actual particle density. Indeed, the subjective VIA score assigned by a well-trained technician correlates substantially linearly with the logarithm of particle density. However, it will be apparent that accuracy of quantitative analysis is strongly dependent upon training and consistency among clinical personnel.

It has also been proposed to measure particle surface concentration employing an optical microscope. However, because particle size is on the same order of magnitude as the wavelengths of visible light (about 400 to 700 nm), and because the particle distribution is often non-uniform, particle counts must be taken over a large enough area of the sample surface to allow statistical averaging to be valid. To perform visual counts over such an area is tedious and time-consuming. Furthermore, the presence of scratches, dust and other imperfections on or in the dipstick, on the same order of magnitude as particle size, contributes to inaccuracy of this method.

It is an object of the present invention to provide a measurement technique which yields an accurate indication of particle concentration, which is inexpensive to implement in immunodiagnostic assays, which yields rapid determination of particle concentration, and which may be readily implemented by relatively unskilled clinical personnel. Another object of the invention is to provide a measurement technique of the described character which provides a digital measure of particle concentration in the range of 0 to 5 and is thus correlated with the manual VIA test score method previously described.

A more general object of the invention is to provide an accurate and inexpensive method of optically measuring concentration of particles on a medium or carrier having particle sizes on the same order of magnitude as the measurement light wavelength, and to provide apparatus for implementing such method.

BRIEF DESCRIPTION OF THE DRAWINGS

The invention, together with additional objects, features and advantages thereof, will be best understood from the following description, the appended claims and the accompanying drawings in which:

FIG. 1 is a functional block diagram of test apparatus in accordance with a presently preferred embodiment of the invention;

FIG. 2 is a schematic diagram of system optics illustrated functionally in FIG. 1;

DETAILED DESCRIPTION OF PREFERRED EMBODIMENTS

Figure 3:
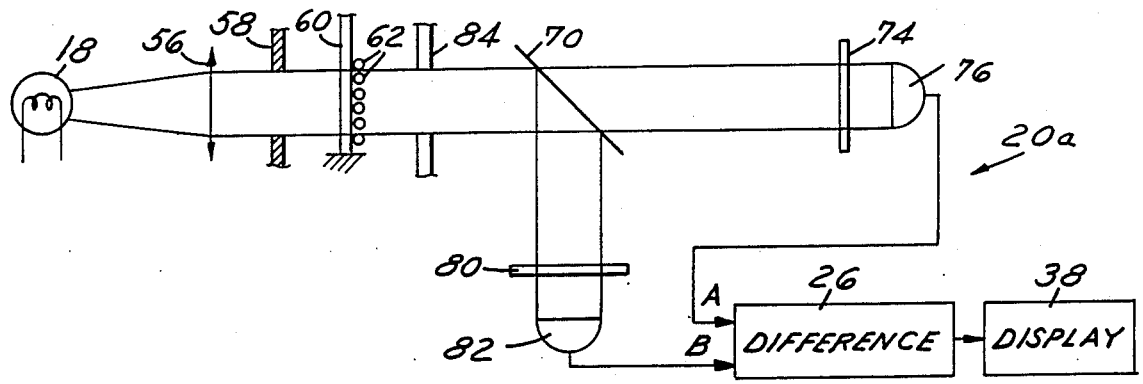
FIG. 3 is a schematic diagram of test apparatus in accordance with a modified embodiment of the invention.

FIG. 1 illustrates a presently preferred embodiment 10 of test apparatus in accordance with the invention as comprising a lamp power supply 12 coupled by the normally-open contact 14 of a relay 16 to the lamp 18 (FIG. 2) of the test apparatus optical system 20 (FIGS. 1 and 2). Optical system 20 provides a pair of electrical outputs A and B to corresponding amplifiers 22, 24, the outputs of which are fed to a comparator 26 which computes the difference (A-B). The output of comparator 26 is fed to a summing junction 28 at which the zero adjustment or offset 30 is added thereto, and thence to a linear amplifier 32 having gain control by span adjustment 34. The output of amplifier 32 is fed through an analog-to-digital converter 36 to an LCD display 38 in a signal range between displays of "0.00" and "5.00" at display 38.

A power supply 40 for the apparatus circuitry is connected through the normally-open contacts of an operator READ pushbutton 42 to a timer 44 which drives the coil 46 of relay 16 for a preselected time duration, such as eight seconds. Pushbutton 42 also feeds power to a second timer 48 which enables update at display 38 for a time duration less than the duration of timer 44, such as seven seconds. Power supply 40 is also connected through a normally-open CALIBRATE switch 50 to an amplifier 52, the output of which drives relay coil 46 and updates LCD display 38 independently of timers 44, 48. Thus, during a calibration operation, switch 50 is closed so as to energize the optical system, and zero adjust 30 is manipulated with a blank dipstick in the test apparatus until display 38 reads "0.00." A second dipstick of known particle density in then placed in the test apparatus, and span adjust 34 is manipulated until the corresponding VIA number is indicated at display 38. Switch 50 is then returned to the normally-open condition, and apparatus 10 is ready for normal operation.

FIG. 2 illustrates optical system 20 in greater detail as including lamp 18 positioned between a reflector 54 and a collimating lens 56 for directing energy at visible wavelengths through an aperature 58. A dipstick or carrier strip 60, having surface particles 62 whose concentration is to be measured, is removably positioned against a stop 63 or other suitable locating means such that collimated light from lamp 60 is directed onto particles 62. Carrier 60 in the embodiment of FIG. 2 is of suitable translucent construction such as glass or plastic, the latter being preferable in terms of cost and biological compatability. Particles 62 preferably comprise spherical beads of translucent latex composition, as taught by above-noted copending application Ser. No. 898,874, the disclosure of which is incorporated herein by reference for background of the preferred implementation of the present invention. However, as will become apparent from the discussion to follow, other particle geometries and compositions, spherical or non-spherical, translucent or opaque, may as readily be employed because the present invention utilizes the phenomenon of light scattering by the particles, rather than absorption or reflection by the particles, for concentration measurement purposes.

A collecting lens 64 is spaced from aperature 58 across dipstick 60 and has a central opaque obscuration 66 aligned with and generally corresponding in size to the opening in aperature 58 for blocking direct transmission of light from lamp 18 through dipstick 60 and particles 62. However, light rays scattered by particle 62 at an angle to the main beam axis bypass obscuration 66 and are fed by lens 64 to a second lens 68 for focusing the light energy onto detector cells. In the preferred embodiment of FIG. 2, the acceptance angle of lens 64 and obscuration 66 for energy scattered by particles 62 is in the range of 20° to 35°, and most preferably in the range of 20° to 30°. A beamsplitter 70 is positioned to intercept light focused by lens 68 and to transmit a portion of such light through a lens 72 and a filter 74 onto a photodetector 76, while reflecting a second portion through a second lens 78 and filter 80 onto a second photodetector 82. Photodetectors 76, 82 provide the output signals A and B to amplifiers 22, 24 in FIG. 1.

FIG. 3 illustrates a modified embodiment 20a of system optics in accordance with the invention. The primary difference between optics 20a in FIG. 3 and optics 20 of FIG. 2 lies in disposition of a second aperature 84 of suitable opaque construction adjacent to the test position of dipstick 60 and aligned with aperature 58 for thus passing to beamsplitter 70 only light transmitted through dipstick 60 and particles 62, and blocking light scattered by the particles. Thus, the preferred embodiment of system optics 20 illustrated in FIG. 2 directly measures light scattered by particles 62, whereas the alternative embodiment of system optics 20a in FIG. 3 measures scattered light indirectly—i.e. as a funtion of light transmitted directly through the dipstick and particles and therefore not scattered by the particles. It is anticipated that the embodiment illustrated schematically in FIG. 3 would be implemented using fiber optics of controlled acceptance angle. Both of the embodiments of FIGS. 2 and 3 are amenable to implementation in conjunction with reflective rather than translucent dipsticks 60, whereby the system electronics is responsive directly to light energy reflected by the dipstick and scattered by the particles in the reflected-light analog to FIG. 2, or light energy reflected by the dipstick and not scattered by the particles in the reflective-light analog to FIG. 3.

In general operation of the embodiment of FIGS. 1 and 2, a portion of the light from source 18 is scattered by particles 62 according to Mie scattering theory, a portion is transmitted past the particles, and a portion is absorbed. The scattered light—i.e., the portion not directly transmitted or absorbed—is directed through filters 74,80 onto detectors 76,82. Transmission wavelengths of filters 74,80 are selected in conjunction with particle size and index of refraction such that variation of the Mie scattering extinction coefficient results in preferential scattering as between the wavelengths of filters 74,80. Particle concentration is indicated at display 38 as a function of such scattering differential. It will be appreciated, of course, that means other than beamsplitter 70 and filters 74,80 may be provided for directing or deflecting light at selected wavelengths onto detectors 76,82. It will also be appreciated that the principles of the invention find general application for measuring concentration of particles on or in any suitable medium.

Figure 4:
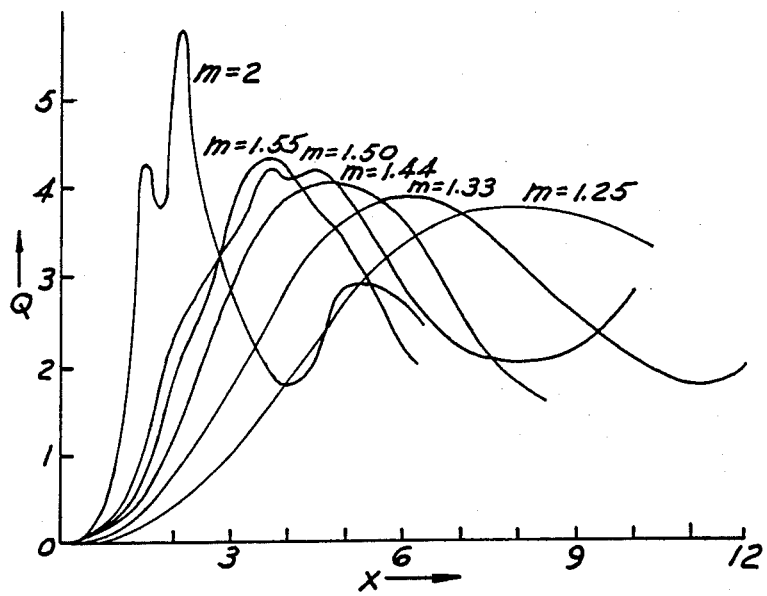
FIGS. 4 and 5 are graphic illustrations useful in explaining theory and operation of the invention.
Figure 5:
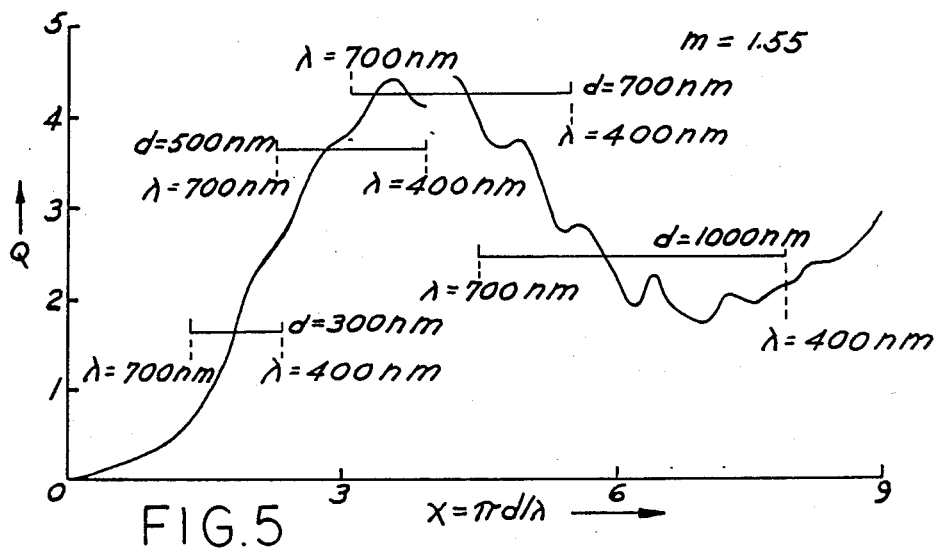

FIG. 4 is a graphic illustration of Mie scattering extinction coefficient Q versus the variable x for several differing refractive indices m, with the variable x for spherical particles being equal to pi times the ratio of particle diameter d to wavelength lambda. FIG. 5 is an expanded illustration of the extinction curve for an index of refraction m equal to 1.55, the approximate index of latex particles. In general, Mie scattering describes the scattering of light by particles for which $x \leq 25$. For $x \geq 25$, the laws of classical geometric optics apply. FIG. 5 also illustrates the range of scattering for visible light (about 400 to 700 nm) at each of several particle diameters d equal to 300 nm, 500 nm, 700 nm and 1000 nm (1 μm). Thus, for a 300 nm diameter particle, blue light (400 nm) is preferentially scattered, while for a 700 nm particle, red light (700 nm) is scattered more strongly.

As shown in FIGS. 4 and 5, each of the extinction curves is characterized by an initial portion in which extinction coefficient Q varies essentially monotonically with x up to a peak, followed by a series of oscillations in which extinction coefficient Q asymptotically approaches the value of about 2 at x equal to about 25. It is preferable in accordance with the present invention to select particle size and refractive index, in conjunction with light wavelengths, such that measurements are performed along the initial or monotonic portion of each curve. For particles having an index of refraction m equal to two, this range extends up to about $x = 1.6$, while for particles with $m = 1.25$, x can range up to about 8. Thus, for particles having a refractive index of 1.25, measurements can be performed in the visible light range up to a particle diameter of about 1 μm, while for latex particles having a refractive index of about 1.55, optimum size for measurement in the visible range is about 500 nm. For accuracy and resolution, as previously noted, preferred minimum size for immunodiagnostic assay purposes is about 300 nm. Throughout the range of 300 to 500 nm, as shown in FIG. 3, blue light (400 nm) is preferentially scattered as compared with red (700 nm).

As particle size x diminishes below a value of unity, the scattering process reduces to so-called Rayleigh scattering, the scattering of light from a point particle. In this regime, the extinction coefficient is greatly reduced from its value in the Mie scattering regime, as can be seen from FIGS. 4 and 5. On the other hand, as the particle size is reduced, the rate at which the test particles diffuse through the test solution to the capture surface is greatly enhanced. Thus, the choice of an optimum particle size is based on a trade-off between desire to implement a rapid test, which would suggest a smaller particle, and desire to scatter light efficiently, which would suggest a larger particle size. A further consideration stems from the fact that, as the particle diameter increases, the angular distribution of the scattered light becomes more complex. At small values of particle size x, the pattern is more nearly isotropic in space. As size x increases, more maxima and minima are observed in the angular distribution. This further complicates interpretation of scattering data for larger particles. All of these considerations suggest use of particles of refractive index of approximately 1.55, and diameters in the range of 300 to 500 nm.

Thus, in the preferred application of the invention for measuring concentration of latex particles 20 (m=1.55) in the size range of 300 to 500 nm, one filter 26 may have a narrow passband centered at the red end of the visible spectrum (about 700 nm), while the other filter 30 has a narrow passband centered at the blue end of the spectrum (about 400 nm). By employing the difference between two measurement wavelengths, effects due to slight changes in orientation of carrier 18 are cancelled. Furthermore, scratches, dirt and other imperfections on carrier 18 scatter relatively independently of wavelength because of random distribution of scattering center size. Thus, comparison at two wavelengths cancels such background effects. For purposes of qualitative and quantitative calibration in the preferred application of the invention to immunodiagnostic assays, it is preferable to employ an essentially monodisperse distribution of particles 20.

The invention claimed is:

1. A method of measuring concentration of particles of size not greater than one micrometer, said method comprising the step of:
    (a) directing light energy through a test medium containing said particles,
    (b) measuring intensity of light energy transmitted through said medium simultaneously at two wavelengths having differing extinction coefficients as a function of particle size and wavelength, and
    (c) indicating particle concentration as a function of a difference between said intensities measured in said step (b).

2. A method of measuring concentration of particles of size on the order of magnitude of the wavelengths of visible light (400 to 700 nm), said method comprising the steps of:
    (a) providing a test medium containing particles of predetermined refractive index and having a particle size distribution such that the extinction coefficient of visible light scattered by said particles varies essentially monotonically as a function of the ratio of particle size to light wavelength,
    (b) directing visible light energy onto said medium,
    (c) measuring intensity of light scattered from said medium at two differing visible wavelengths, and
    (d) indicating particle concentration as a function of intensities measured in said step (c).

3. The method set forth in claim 2 wherein said intensities are measured simultaneously in said step (c).

4. The method set forth in claim 3 wherein said step (d) comprises the step of indicating particle concentration as a function of a difference between said intensities.

5. Apparatus for measuring surface concentration of particles on a carrier, said particles having a preselected essentially monodisperse size distribution not greater than one micrometer and a predetermined index of refraction, comprising
    a source of white light,
    means for positioning a carrier such that light from said source is directed onto particles on said carrier,
    means for simultaneously measuring intensity of light scattered by said particles at two differing wavelengths of said light between which the extinction coefficient of visible light scattered by said particles of said predetermined index of refraction varies essentially monotonically as a function of the ratio of particle size to light wavelength, and
    means for indicating surface concentration of said particles on said carrier as a function of a difference between said intensities.

6. The apparatus set forth in claim 5 wherein said particles have a refractive index equal to about 1.55, and wherein said particles have a size between 300 and 500 nm.

7. The apparatus set forth in claim 6 wherein said two wavelengths are at substantially 400 and 700 nm.

8. The apparatus set forth in claim 5 wherein said means for indicating surface concentration comprises digital display means, and means for driving said display to read in the range of zero to five as a linear function of log of particle concentration.

9. The apparatus set forth in claim 8 wherein said display-driving means includes means for selectively adjusting zero and span of said display-driving means.

10. The apparatus set forth in claim 8 wherein said intensity-measuring means comprises means for collecting light scattered by said particles while blocking direct transmission from said source.

11. The apparatus set forth in claim 8 wherein said intensity-measuring means comprises means for collecting light energy transmitted directly past said particles from said source, while blocking light energy scattered by said particles, and means for measuring said scattered light indirectly as a function of light transmitting past and not scattered by said particles.

12. A method of measuring concentration of particles of size not greater than one micrometer, said method comprising the steps of:
    (a) providing said particles in a preselected essentially monodisperse size distribution not greater than one micrometer and of predetermined index of refraction,
    (b) directing light energy onto the particles,
    (c) measuring intensity of light energy scattered by the particles at first and second wavelengths selected in conjunction with said preselected size distribution and index of refraction such that differing scattering extinction coefficients are exhibited at said wavelengths,
    (d) comparing intensities measured in said step (c), and
    (e) indicating concentration of the particles as a function of such comparison.

13. The method set forth in claim 12 wherein said intensities are measured simultaneously in said step (c), and wherein said step (e) comprises the step of indicating concentration as a function of a difference between said intensities.

14. The method set forth in claim 13 wherein said step (c) comprises the step of indirectly measuring intensity of light scattered by the test particles by measuring intensity of light transmitted past the particles.

15. The method set forth in claim 13 wherein said wavelengths are selected in conjunction with said preselected particle size distribution and predetermined index of refraction such that said scattering extinction coefficient varies essentially monotonically between said wavelengths.

16. The method set forth in claim 15 wherein said wavelengths are in the visible light energy spectrum.

17. The method set forth in claim 16 wherein said particles comprise an essentially monodisperse distribution in the range of 300 to 500 nm, and wherein said wavelengths are selected at the red and blue ends of the visible spectrum respectively.

* * * * *